United States Patent [19]

Conston et al.

[11] Patent Number: 5,332,626
[45] Date of Patent: Jul. 26, 1994

[54] PORES OF CONTROLLED GEOMETRY ON A THERMOPLASTIC POLYMER

[75] Inventors: Stanley R. Conston, San Carlos; Glenn C. Buchanan, Belmont, both of Calif.

[73] Assignee: Vitaphore Corporation, Menlo Park, Calif.

[21] Appl. No.: 8,278

[22] Filed: Jan. 25, 1993

Related U.S. Application Data

[62] Division of Ser. No. 580,947, Sep. 11, 1990, Pat. No. 5,213,742.

[51] Int. Cl.$^5$ .............................................. B32B 9/00
[52] U.S. Cl. .................................. 428/409; 428/141; 428/156; 428/304.4; 428/310.5; 428/314.2; 428/315.5; 428/412; 428/423.1; 428/480; 521/155; 521/182; 523/114; 525/937
[58] Field of Search ................ 428/141, 156, 304.4, 428/310.5, 314.2, 315.5, 412, 423.1, 480, 409; 521/155, 182; 523/114; 525/937

[56] References Cited

U.S. PATENT DOCUMENTS

| | | | |
|---|---|---|---|
| 3,057,098 | 10/1962 | Gabriel | 264/340 |
| 3,384,696 | 5/1968 | Makansi | 264/321 |
| 3,809,600 | 5/1974 | Larson | 161/109 |
| 3,865,574 | 2/1975 | Long | 75/479 |
| 3,959,546 | 5/1976 | Hill | 428/141 |
| 4,199,864 | 4/1980 | Ashman | 433/175 |
| 4,384,047 | 5/1983 | Benzinger | 521/64 |
| 4,493,748 | 1/1985 | Cross | 156/79 |
| 4,559,254 | 12/1985 | Suzuki | 428/131 |
| 4,579,698 | 4/1986 | Meyering | 264/41 |
| 4,609,584 | 9/1986 | Cutler | 428/156 |
| 4,661,394 | 4/1987 | Curry | 428/212 |
| 4,698,372 | 10/1987 | Moss | 521/145 |
| 4,726,989 | 2/1988 | Mrozinski | 428/315.5 |
| 4,751,127 | 6/1988 | Pinkston et al. | 428/141 |
| 4,778,634 | 10/1988 | Douglas | 264/22 |
| 4,787,900 | 11/1988 | Yannas | 623/1 |
| 4,801,386 | 1/1989 | Sugimori | 210/680 |
| 4,880,843 | 11/1989 | Stein | 521/98 |
| 4,902,511 | 2/1990 | Kronman | 424/423 |
| 5,028,332 | 7/1991 | Ohnishi | 210/500.34 |
| 5,093,180 | 3/1992 | Morgan | 428/156 |

Primary Examiner—Patrick J. Ryan
Assistant Examiner—Marie R. Macholl
Attorney, Agent, or Firm—Heller, Ehrman, White & McAuliffe

[57] ABSTRACT

A process is provided for manufacturing nonwoven, nonbiodegradable tissue ingrowth-inducing, tissue-interfacing substrates with predetermined oriented uniform pore diameter, pore density and pore depth. Pins are inserted to a predetermined depth into a softened thermoplastic substrate or, heated pins are inserted into the substrate, then removed to form the predetermined pore pattern.

3 Claims, 5 Drawing Sheets

PORES AT 120X, 45DEG TILT

PORES AT 120X, 45DEG TILT

PORES AT 500X, 45DEG TILT

CROSS SECTION, 130X

CROSS SECTION, 500X

"GOOD" PORE AT 1200X, 0DEG TILT

"GOOD" PORE AT 800X, 45DEG TILT

"BAD" PORE AT 800X, 0DEG TILT

"BAD" PORE AT 800X, 45DEG TILT

PORES OF CONTROLLED GEOMETRY ON A THERMOPLASTIC POLYMER

This is a division of application Ser. No. 07/580,947 filed Sep. 11, 1990, now U.S. Pat. No. 5,213,742.

The present invention is directed to a method for producing nonwoven, nonbiodegradable tissue ingrowth inducing, tissue interfacing substrates.

BACKGROUND OF THE INVENTION

Infection is a major concern associated with percutaneous and implant devices and an approach to such problem has recently focused on development of composite collagen-polymer matrices which can accommodate antimicrobial factors and which are compatible with the tissue. One of the problems is to enhance or impart tissue ingrowth properties to the non-degradable polymer matrix of such devices. In a collagen-polymer matrix, the collagen portion is naturally reabsorbed into the host tissues, therefore a viable environment for tissue interfacing with the device substrate (the polymer) is desired. However, if the epithelial tissues do not interface to the implant device, they will begin to propagate toward areas which may increase the chances of infection. For example, if a percutaneous device is an elastomeric cuff around a catheter, if the epithelial tissues do not adhere to the percutaneous cuff, they will begin to propagate down the catheter conduit, forming a sinus tract which may form a pathway for bacterial contamination and potentially serious infection.

It is therefore important to develop methods for creating controlled porosity for the elastomeric substrate which form a component of such percutaneous or implant devices, which improve or impart tissue ingrowth-inducing and tissue-interfacing properties and encourage epithelial growth into the device.

We have found that size, and in particular the shape, of pores on the surface of the elastomeric substrate are important in inducing tissue ingrowth properties. Imperfect pores, i.e. those which may form a circumferential mushroom on the surface surrounding the pore or which do not have smooth flat or slightly domed flat bottom surfaces, are undesirable. It is therefore important to devise a method to form the pores at the desired predetermined pore densities, sizes, and depths in an efficient manner which also achieve the desired pore shapes.

It is therefore an object of the present invention to provide a method for manufacturing a nonwoven, non-degradable tissue ingrowth-inducing, tissue-interfacing substrate with predetermined oriented sizes, pore densities and pore depths.

This and other objects of the invention will be apparent from the following description and from practice of the invention.

SUMMARY OF THE INVENTION

The present invention provides a process for manufacturing a nonwoven, non-degradable tissue ingrowth-inducing, tissue-interfacing substrate with predetermined uniform pore size, pore density and pore depth comprising steps of
  (a) providing a thermoplastic substrate;
  (b) contacting at least a portion of one surface of the substrate with a heated surface for a sufficient period of time and at temperature sufficient to soften the substrate without deformation;
  (c) while the substrate is in a softened state, inserting perpendicularly into the surface of the substrate a plurality of pins, which are at a lower temperature than the substrate, of sufficient external diameter to achieve a predetermined pore size in a pattern sufficient to achieve the predetermined pore density and with sufficient force and displacement to achieve the predetermined pore depth;
  (d) removing the substrate from the heated surface to allow the substrate to cool;
  (e) removing the pins from the substrate;
  (f) optionally, repeating steps (b), (c), (d) and (e) on a different portion of the substrate surface.

In a second embodiment a process for manufacturing a nonwoven, non-degradable tissue ingrowth-inducing, tissue-interfacing substrate with predetermined oriented, uniform pore size, pore density and pore depth is provided comprising the steps of:
  (a) providing a thermoplastic substrate;
  (b) inserting perpendicularly into at least a portion of the substrate heated pins for a period of time for said pins to soften and penetrate the substrate, the pins being of sufficient external diameter to achieve the predetermined pore size in a predetermined pattern sufficient to achieve the predetermined pore density and with sufficient force and displacement to achieve the predetermined pore depth;
  (c) removing the pins from the substrate;
  (d) optionally repeating steps (b) and (c) on a different portion of the substrate.

The preferred thermoplastic substrate produced by these methods is a polyurethane or polyethylene terephthalate having, on the surface or surfaces to be exposed to the tissue, a pore density in the range of about 20 to 10,000 pores per square centimeter; with uniform pores of diameter in the range of about 50 to 500 microns, with the pores characterized by a substantially cylindrical shape. The pores have substantially smooth flat or slightly curved bottom surfaces.

DESCRIPTION OF THE PREFERRED EMBODIMENTS

Figure 1:
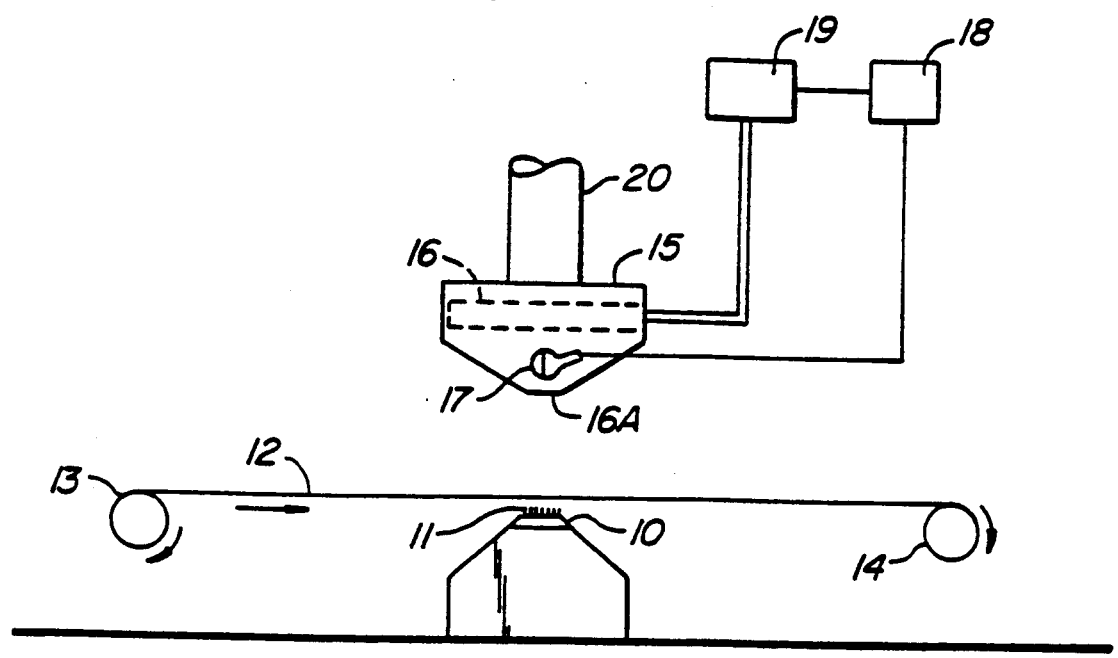
FIG. 1 shows a preferred embodiment apparatus for performing a method according to the present invention.

Referring to FIG. 1, there is shown a preferred apparatus for performing the method in accordance with the present invention. Preferably a stationary pin clamp 10 is utilized having a preselected number of pins 11 of sufficient diameter to produce pores of the desired diameters when perpendicularly pressed into a softened elastomeric substrate 12, fed across the pins by feed roller 13 and take-up roller 14. The pins 11 and substrate 12 are juxtaposed so that the pins will form essentially perpendicular pores on the substrate. A heated anvil 15, is mounted parallel to the pins 11. The anvil 15 contains a heating element 16 and a thermocouple 17 used with temperature controller 18 to, in turn, control the heater power source 19. The substrate 12 (shown as a sheet) is pulled along between, but not in contact with either the anvil face 16A or the pins 11, using a precision advancing mechanism (not shown), such as a lead screw assembly. To perform the process, the heated anvil face 16A (heated to a temperature to achieve softening of the substrate without deforming the substrate) is brought into contact with the substrate 12 by lowering shaft 20. Depending upon the chemical nature of the substrate and the thickness of the substrate, the period of time of this contact will be determined so that the substrate is sufficiently softened to receive the pins. This means that the substrate will be heated to a temperature of about 10° F. or less above its softening point, provided that the temperature is also maintained at least about 5° F. below the melting point of the substrate. This period of time, for a polyurethane sheet of about a thickness of about 0.010 to 0.015" is typically in the range of about 0.5 to 2.5 seconds at a temperature in the range of 170° to 300° F. When the substrate is sufficiently softened, the cool pins 11 are pressed into the opposite surface of the substrate by further lowering of shaft 20 where the depth of the imprint of the pins is controlled by a stop on the press (not shown). Then the anvil is released from the substrate, with the pins 11 still in place, thereby allowing the substrate to cool, and fixing the pore size and shape. This prevents heat buildup which would cause nonuniform pores. The pins 11 remain in the substrate 12 (dwell time) on an average of about 2 seconds and then are withdrawn. The substrate 12 is then moved so that pores may be imprinted on a different area.

If desired, the pins may be used to puncture almost entirely through the substrate, but it is preferred that the pores penetrate to a depth of about 5× to 20× the pore diameter.

Figure 2:
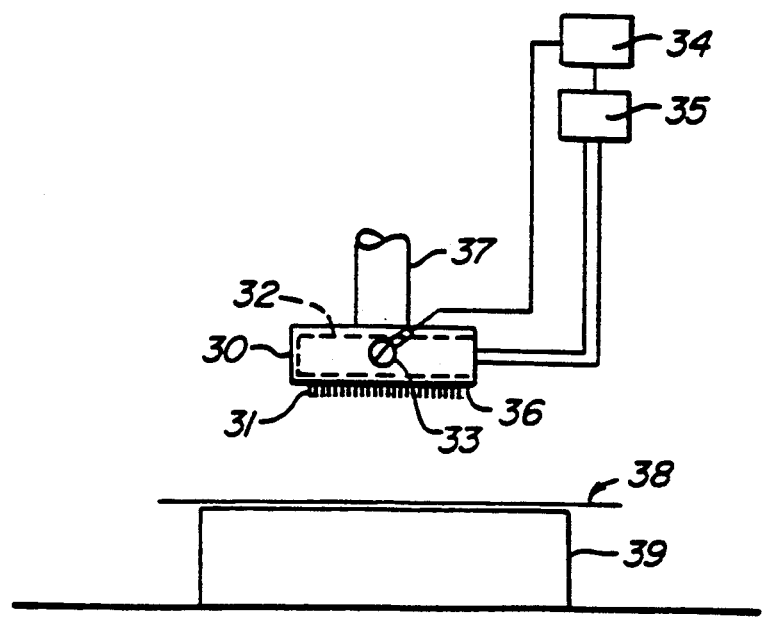
FIG. 2 shows a second embodiment of an apparatus for performing a method according to the present invention.
Figure 3A:
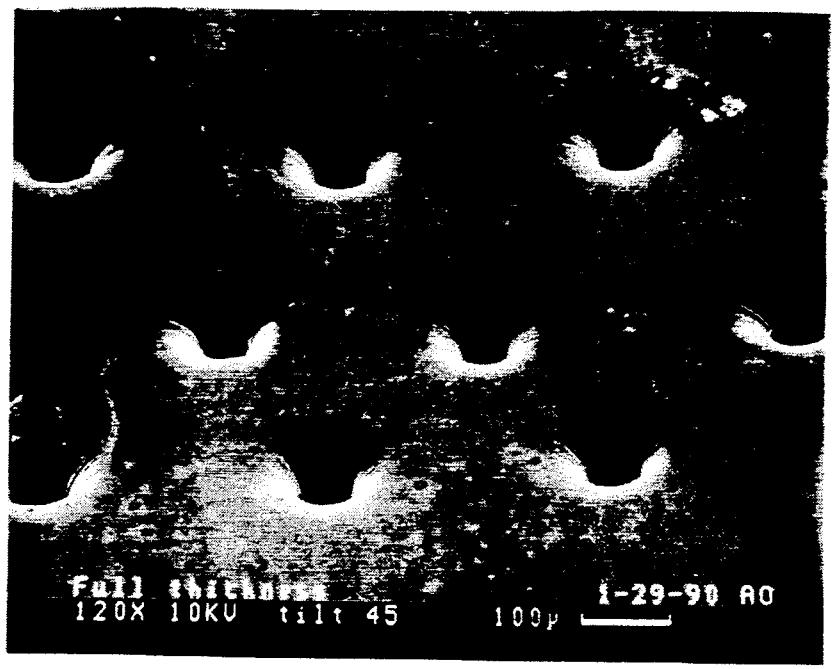
FIGS. 3A and 3B are SEM micrographs of pores made according to the invention at 120× and 500× magnification, respectively, viewed from a 45° tilt.
Figure 3B:
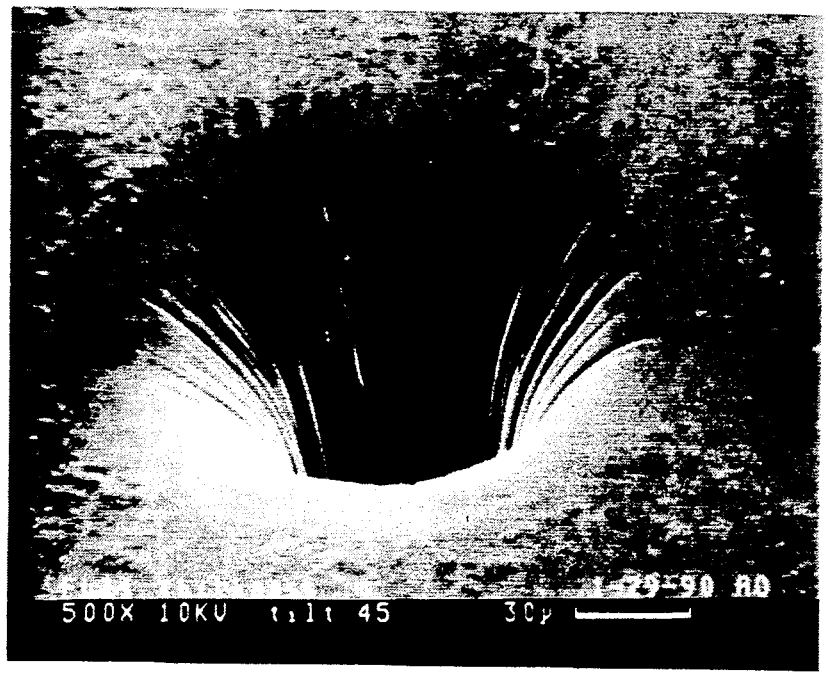

In an alternate embodiment of the invention, referring to FIG. 2, a heated head 30 accommodating a plurality of pins 31 is utilized. The head 30 and pins 31 are heated with an internal heating element 32 located within the head controlled by a thermocouple 33 (or other suitable means of temperature control), which is electrically connected to a temperature controller 34, which, in turn, controls the heater power source 35. A clamping plate 36 fixes the pins in place. The head is used with any appropriate automatic displacement device, such as a linearly controlled shaft 37, to automatically lower it toward the surface of the cool substrate 38 and unheated anvil 39 to form imprints of the pins at a predetermined depth for a predetermined dwell time, then withdrawn. The heated pins 31, while made of a smooth metal, such as stainless steel, are preferably coated with a smooth, heat impervious coating such as a high temperature silicone, so that as the pins are withdrawn they do not extrude unduly large threads of elastomeric material from the pores, thereby changing the pore size and/or shape. The pins should be at a temperature sufficient to soften the substrate, i.e., about 10° F. or less above the softening point. For a polyurethane sheet of 0.015" thickness, the pins should be at a temperature in the range of about 170° to 300° F. and the dwell time should be about 0.5 to 2 seconds.

For tissue ingrowth and tissue implant properties, polyurethanes are the preferred substrates, particularly polyurethane sold under the trade names TECOFLEX (Thermedics, Inc.), BIOMER (Ethicon) and PELLATHANE (Dow Plastics). A second class of preferred elastomeric materials are polyethylene terephthalates, particularly sold under the trade names KODAPAK, TENITE and VALOX by Eastman and GE Plastics. Other suitable thermoplastic materials include, but are not limited to, acrylic and methacrylic polymers or copolymers, acetal homopolymers, acetal copolymers of trioxane and ethylene oxide, epoxy resins, phenylene oxide-based resins (such as, polyphenylene oxide and blends of polyphenylene oxides and styrene resins), polyaryl ethers, polyesters, polyethylene, polypropylene, polysulfones, ethylene polymers (such as ethyl vinyl acetates), and other thermoplastics which are non-degradable and nonwoven.

A useful pore density is in the range of about 20 to 10,000 pores per square centimeter, with the greater number of pores the better. A typical uniform pore diameter with typical tissue ingrowth properties is from about 50 to about 500 microns, but there may be useful pores outside of this range.

Figure 4A:
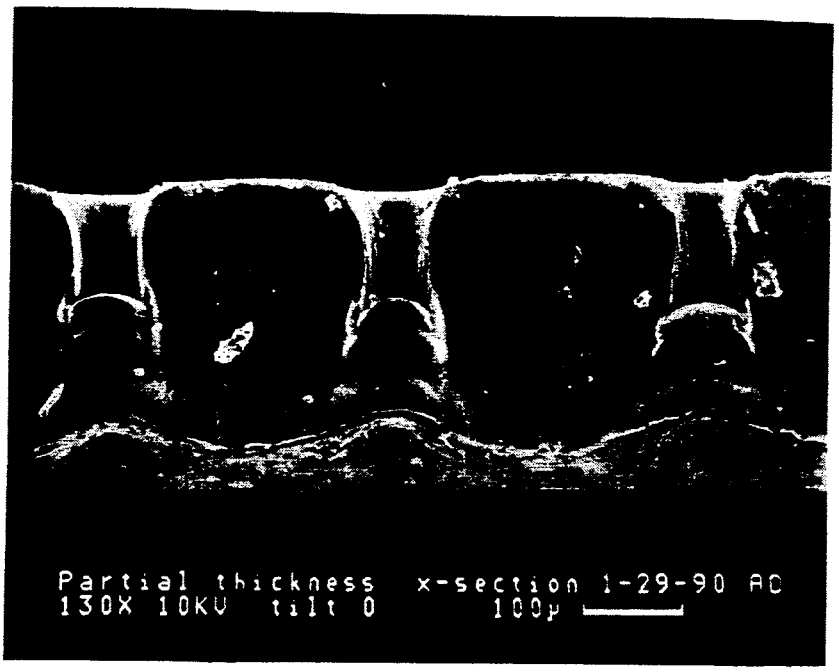
FIGS. 4A and 4B are SEM micrographs of pores made according to the invention at 130× and 500× magnification, respectively, cross-sectional views.
Figure 4B:
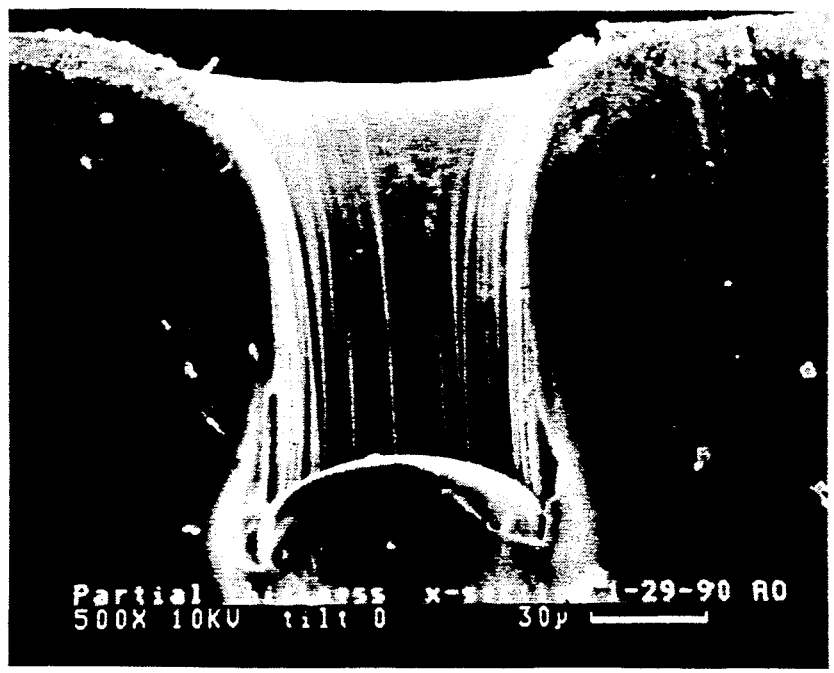

Utilizing the device shown in FIG. 1, a set of samples (polyurethane sheets, 0.3 mm thick) were fabricated having a pore size from 50 to 75 microns and a density of about 1430 pores per square centimeter (Anvil temp. 225° F.; softening contact time 1 sec.; pin dwell time 2 sec.) One set was at pore depths about halfway through the polymer and another set had depths nearly all the way through the polymer. The samples were examined by a scanning electron microscope, the results of which are shown in FIGS. 3A, 3B, 4A, 4B. There are practically 100% good pores shown (FIGS. 3A and 3B), with the cross-sections of the pore samples having nearly straight cylindrical walls with nearly flat floors which in some cases were slightly curved upwards and radiused topped edges (FIGS. 4A and 4B).

Figure 5A:
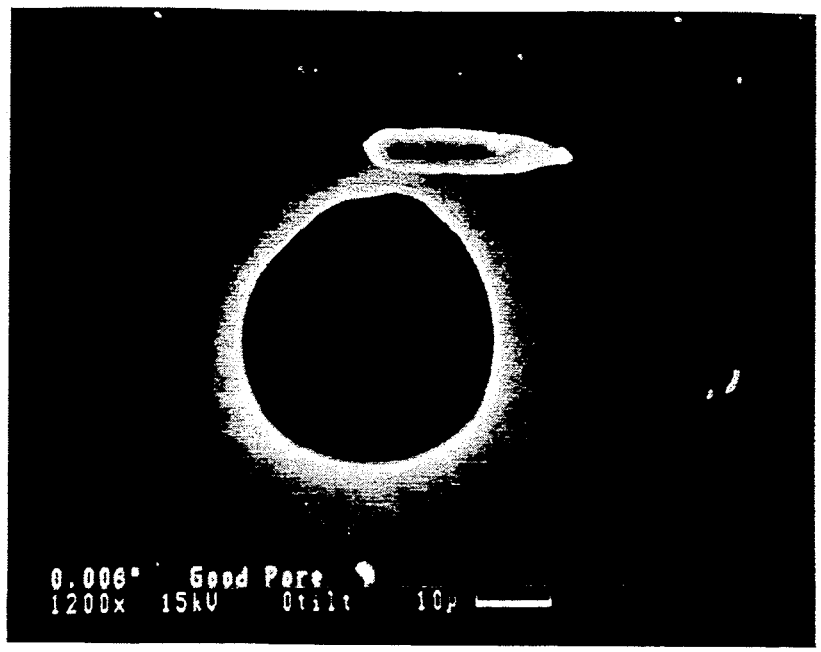
FIGS. 5A and 5B are SEM micrographs of a pore made according to the invention at 1200× and 800× magnification, respectively, at 0° and 45° tilts, respectively.
Figure 5B:
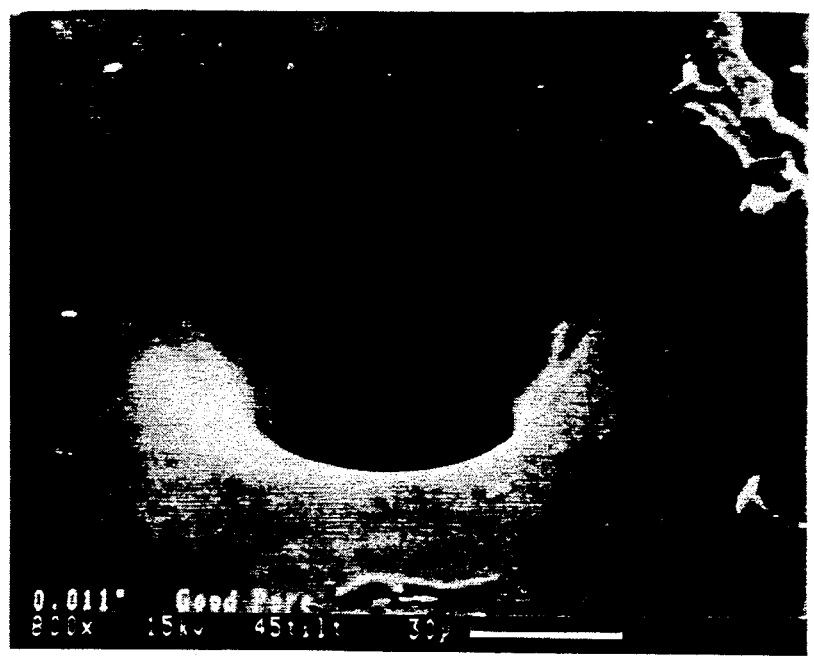
Figure 5C:
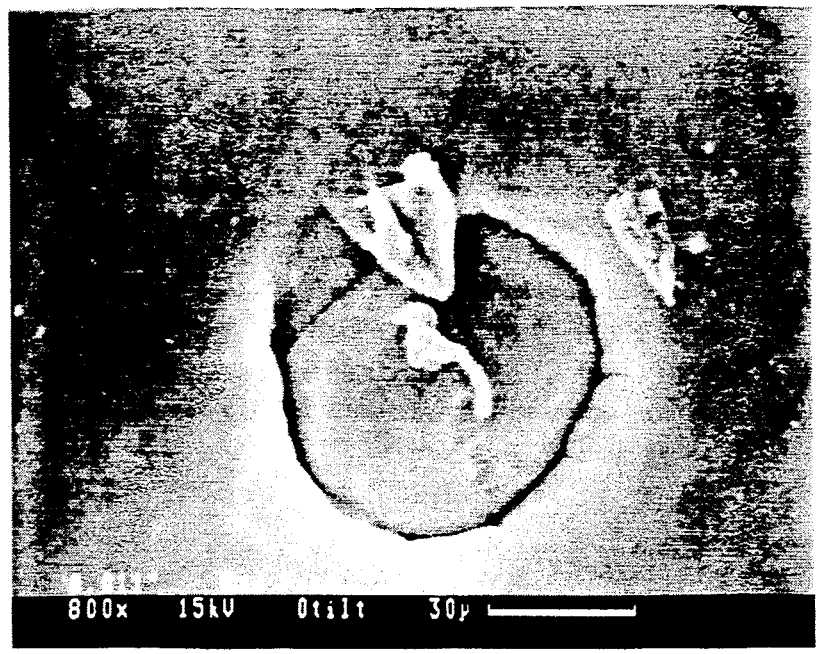
FIGS. 5C and 5D are SEM micrographs of a pore made according to the invention with slight imperfections (extrusions) at 800× magnification, viewed at 0° and 45° tilts, respectively.
Figure 5D:
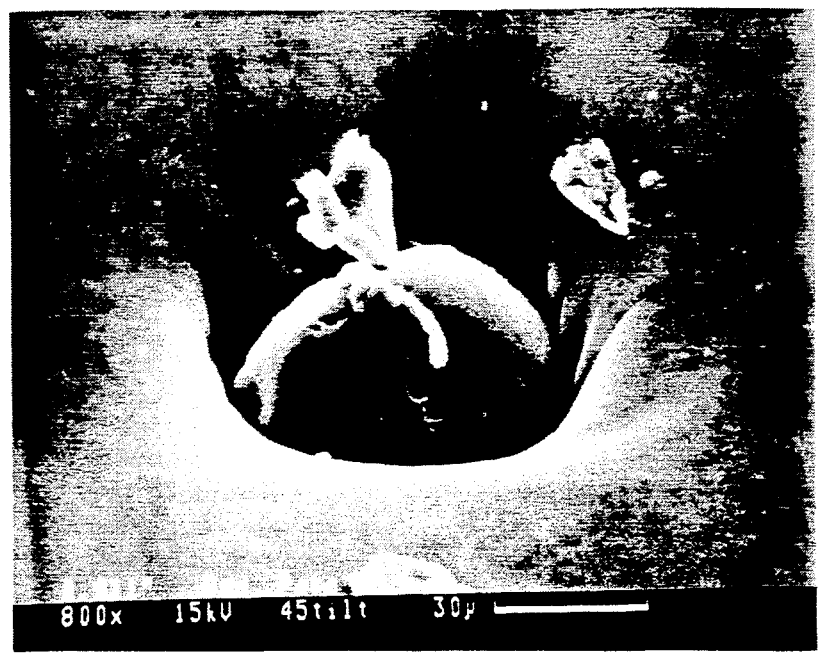

Pores made using the device in FIG. 2 are shown in FIGS. 5A–5D, with sample pore sizes 280 microns, 220 microns and 160 microns, on polyurethane sheets. Half-depth pores were formed (pin temp. 200° F., dwell time 2 sec). About 28% of the pores were perfect pores (FIGS. 5A and 5B). Many of the pores showed some melted polymer material adhering to the imprinting pin and extruded back to the pore (FIGS. 5C and 5D).

The following examples are provided by way of illustration and are not intended to limit the invention in any way.

EXAMPLE 1

Flat sheets of polyurethane in five different porosity configurations were made using the device of FIG. 2, using pin temperature of 200° F. and dwell time of 2 sec. The configurations are as follows: two systems with a pore size of 280µ, one with a density of pores of 36 cm$^2$ and the other of 320 cm$^{-2}$; one system with a pore size of 220µ and a density of 220 pores cm$^{-2}$; and two systems with a pore size of 160µ, one with a density of 120 pores cm$^{-2}$ and the other a density of 1000 pores cm$^{-2}$.

Two 1 cm×2 cm polyurethane sheets (0.3 mm thick) of each porosity configuration were implanted in six white New Zealand rabbits, for a total of ten implants per animal. Four incisions were made into the dorsum of each rabbit (two on each side). Underneath each of the incisions, two or three separate subcutaneous pockets were created allowing for a total of five implants per side. Three rabbits were sacrificed at 2 weeks and three rabbits at 4 weeks. Implants were removed taking care not to damage the fibrous capsule, by cutting a thick slice of skin and subcutaneous tissue around the implant. These samples were fixed in formalin, histologically processed, embedded in paraffin, sectioned 5μ thick and placed on microscope slides. All sections were stained with H&E, PAS, trichrome, nonspecific esterase, and acid phosphates. Two sections of each type of stain were prepared for light microscopic evaluation.

In order to achieve the most efficient evaluation of each implant, the capsule was divided into 3 layers—inner, middle, and outer. The inner layer is the inflammatory layer of cells immediately surrounding the implant. The middle layer is the center of the capsule which consists mainly of collagen and fibroblasts. The outer layer is the area farthest from the implant usually dominated by blood vessels.

During microscopic observation, the thickness of the capsule and inner inflammatory layer were measured around the entire perimeter of the implant. Measurements of the distance from implant to the closest blood vessels were obtained. Quantitative measurements of enzyme, macrophage, and fibroblast activity, as well as blood vessel population, were taken at randomly chosen areas in each of the 3 capsule layers. Using polarized light, each of the capsule layers was inspected for collagen fiber quantity, orientation and density.

Tables I, II, and III are qualitative comparisons of the inner, middle and outer layers of each capsule surrounding their respective implant. A scale of 0–5 was used with a 5 indicating the most, thickest, or densest of the characteristic being compared.

Using the qualitative data for each of the five implant types, a ranking of implants was determined based on the most beneficial characteristics for a percutaneous tissue-interfacing material to exhibit. In Table IV, implants are ranked from the porosity configuration with the most to the one with the least desirable behavior for the characteristics of capsule thickness, vascularity, macrophage and fibroblast content, and collagen density and orientation. Similar to the other tables, each capsule layer is compared separately.

TABLE 1

| | INNER-INFLAMMATORY LAYER | | | | |
|---|---|---|---|---|---|
| Implant | +Capsule Thickness | Blood Vessel | Macro-phages | Fibro-blasts | Collagen |
| 4075-36 | 4 | 0 | 1 | 2 | 4 |
| 4075-36 | 5 | 0 | 4–5 | 2 | 1 |
| 4074-120 | 1 | 0 | 2 | 3–4 | 1 |
| 4075-120 | 4 | 0 | 3–4 | 1 | 0 |
| 4071-225 | 2 | 0 | 3–4 | 3 | 1 |
| 4074-225 | 3 | 0 | 5 | 1 | 1 |
| 4071-320 | 1 | 0* | 4 | 3–4 | 2 |
| 4075-320 | 3 | 0 | 1 | 2 | 1 |
| 4071-1000 | 1 | 0* | 4 | 3–4 | 0 |
| 4074-1000 | 2 | 0 | 1 | 3–4 | 1 |

*Possible thin layer near the surface
+ Thickness of inflammatory layer

TABLE II

| | MIDDLE-COLLAGEN LAYER | | | | |
|---|---|---|---|---|---|
| Implant | +Capsule Thickness | Blood Vessel | Macro-phages | Fibro-blasts | Collagen |
| 4075-36 | 3 | 0 | 1 | 3 | 4 |
| 4075-36 | 1 | 0 | 1 | 3–4 | 3 |
| 4074-120 | 2 | 2 | 1 | 3–4 | 2 |
| 4075-120 | 1 | 0 | 2 | 2–3 | 2 |
| 4071-225 | 4 | 4 | 3–4 | 1 | 3 |
| 4074-225 | 5 | 5 | 1 | 2 | 2 |
| 4071-320 | 3 | 4 | 3–4 | 2 | 3 |
| 4075-320 | 4 | 1 | 2 | 2 | 3 |
| 4071-1000 | 2–3 | 4 | 2 | 2 | 1 |
| 4074-1000 | 5 | 2 | 1 | 3 | 2 |

+ Density of collagen in the middle layer

TABLE III

| | OUTER-BLOOD VESSEL LAYER | | | | |
|---|---|---|---|---|---|
| Implant | +Capsule Thickness | Blood Vessel | Macro-phages | Fibro-blasts | Collagen |
| 4075-36 | 0 | 1 | 4 | 1 | 5 |
| 4075-36 | 0 | 1 | 4 | 1 | 4 |
| 4074-120 | 1 | 3 | 4 | 1 | 4 |
| 4075-120 | 0 | 2 | 3 | 1 | 4 |
| 4071-225 | 3 | 3 | 3–4 | 2 | 4 |
| 4074-225 | 5 | 5 | 3 | 4 | 4 |
| 4071-320 | 2 | 2 | 4 | 2 | 3 |
| 4075-320 | 0 | 3 | 2 | 2 | 3 |
| 4071-1000 | 2 | 3 | 2 | 2 | 2 |
| 4074-1000 | 5 | 5 | 2 | 4–5 | 4 |

+ Thickness of blood vessel layer

TABLE IV

RANKING OF IMPLANTS ACCORDING TO MOST DESIRABLE CHARACTERISTICS IN EACH OF THE THREE LAYERS OF THE CAPSULE

| Pore Size | Capsule Thickness | Blood Vessel | Macro-phages | Fibro-blasts | Collagen/Orient |
|---|---|---|---|---|---|
| 1000 | 1,3,2 | 1,2,1 | 1,2,1 | 1,3,1 | 2,5,4 |
| 320 | 2,3,3 | 1,3,3 | 1,5,2 | 2,4,3 | 3,2,4 |
| 225 | 3,5,1 | 5,1,1 | 5,4,2 | 3,5,1 | 1,3,2 |
| 120 | 3,1,4 | 5,4,3 | 1,2,4 | 3,1,4 | 3,3,2 |
| 36 | 5,1,5 | 5,5,5 | 1,1,5 | 3,1,4 | 3,1,1 |

Under each column, the three numbers represent the ranking of each implant in the inner, middle, outer layer.
A "1" signifies the implant with the highest ranking and "5" the implant with the lowest ranking.

EXAMPLE 2

Flat sheets of TECOFLEX polyurethane in 2 different porosity configurations were made using a device as shown in FIG. 1 (anvil temp. 225° F., contact time 1 sec, pin dwell time 2 sec). Both had pores of 50–75μ at a density of 1430/cm². The only difference between the two different implant types is their pore depth, one with half depth pores and the other with full depth pores.

Six 1 cm×3.5 cm sheets of each porosity configuration were implanted in two white New Zealand rabbits, for a total of twelve implants per animal. Four incisions were made into the dorsum of each rabbit (two on each side). Underneath each of the incisions, three separate subcutaneous pockets were created allowing for a total of six implants per side. One rabbit was sacrificed at 17 days and one rabbit at 32 days. Implants were removed taking care not to damage the fibrous capsule, by cutting a thick slice of skin and subcutaneous tissue around the implant.

The histological portion of each implant was infiltrated in a vacuum at 37° C. with a graded series of gelatin solution, up to 25%, at which time they were embedded in 25% gelatin. The embedded samples were frozen in liquid nitrogen and sectioned on a cryostat. Because the polymer never became frozen like the surrounding tissue, rarely was the implant itself kept in the sections.

Two sections of each sample have been stained with H&E and trichrome and microscopically analyzed. During microscopic observation, the thickness of the capsule was measured. Quantitative measurements of macrophage and fibroblast activity, as well as blood vessel population, were taken at randomly chosen areas in both the capsule and pores. Using polarized light, the capsule and pores were inspected for collagen fiber quality, orientation and density.

After cryostat sectioning was complete, a portion of the implant was left uncut. A few of these leftover samples were stained with tolulene blue and viewed under a stereomicroscope to try and observe the ingrowth of collagen into the pores.

Histological slides of the 17 day samples show areas of what appears to be ingrowth. The half depth pore samples of this time period have an average capsule thickness of 125-175 μm, little macrophage response near the implant, approximately 18% volume percentage of fibroblasts, and a neutrophil and macrophage response on the outer radius of the capsule. The full pore samples had capsule thicknesses that ranged from 50-175 μm, approximately 15% volume percentage of fibroblasts, little macrophage response near the implant, but heavy neutrophil and macrophage response on the outer radius of the capsule. Both the full depth and half depth pore samples seemed to have vessels running parallel to the implant as close as 25 μm and less.

On the 32-day samples, the half depth pore samples have an average capsule thickness of 150 μm, approximately 25% volume percentage of fibroblasts, and the same type of neutrophil and macrophage response on the outer radius of the capsule. The full depth pore samples had average capsule thicknesses of 175 μm on one side and 250 μm on the other side. There was an approximately 33% volume percentage of fibroblasts, and the same type of neutrophil and macrophage reaction on the outer perimeter of the capsule. Both the full and half depth pore samples had the same type of parallel vessels as the 17 day samples with a heavier vessel population. These 32 day samples also seemed to have a denser, more mature collagen matrix than that of the 17 day samples.

What is claimed is:

1. A nonwoven, nonbiodegradable tissue ingrowth-inducing, tissue-interfacing thermoplastic substrate having surface pores of a substantially uniform density, diameter and depth, said pore density in the range of about 20 to 10,000 pores per square centimeter; said uniform pore diameter being in the range of about 50 to 500 microns, said pores characterized by substantially cylindrical shape with substantially flat or slightly curved bottom surfaces.

2. A substrate according to claim 1 comprising polyurethane.

3. A substrate according to claim 1 comprising polyethylene terephthalate.

* * * * *